(12) United States Patent
Chen et al.

(10) Patent No.: US 12,036,280 B2
(45) Date of Patent: Jul. 16, 2024

(54) HIGH CONCENTRATION PROTEIN FORMULATION

(71) Applicant: Regeneron Pharmaceuticals, Inc., Tarrytown, NY (US)

(72) Inventors: Hunter Chen, New York, NY (US); Erica Schlesinger, Sisters, OR (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/690,956

(22) Filed: Nov. 21, 2019

(65) Prior Publication Data

US 2020/0155678 A1 May 21, 2020

Related U.S. Application Data

(60) Provisional application No. 62/770,337, filed on Nov. 21, 2018.

(51) Int. Cl.
| | | |
|---|---|---|
| *A61K 39/395* | (2006.01) | |
| *A61K 47/10* | (2017.01) | |
| *A61K 47/14* | (2017.01) | |
| *A61K 47/22* | (2006.01) | |
| *A61K 47/26* | (2006.01) | |

(52) U.S. Cl.
CPC ........ *A61K 39/39591* (2013.01); *A61K 47/10* (2013.01); *A61K 47/14* (2013.01); *A61K 47/22* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 2002/0065399 A1* | 5/2002 | Stevenson | ............ | A61K 9/0075 |
| | | | | 530/399 |
| 2011/0223208 A1* | 9/2011 | Hill | .......................... | A61K 9/10 |
| | | | | 424/400 |
| 2012/0076800 A1 | 3/2012 | Dai et al. | | |
| 2012/0230913 A1* | 9/2012 | Johnston | ................ | C07K 16/00 |
| | | | | 424/1.49 |
| 2013/0309226 A1* | 11/2013 | Armstrong | ....... | A61K 39/39541 |
| | | | | 424/133.1 |

FOREIGN PATENT DOCUMENTS

| | | |
|---|---|---|
| EP | 2683403 A1 | 1/2014 |
| EP | 2849723 A1 | 3/2015 |
| WO | WO 2008/157409 A1 | 12/2008 |
| WO | WO 2012/121754 A1 | 9/2012 |
| WO | WO 2013/173687 A1 | 11/2012 |
| WO | WO 2014/093203 A1 | 6/2014 |
| WO | WO 2016/109822 A1 | 7/2016 |

OTHER PUBLICATIONS

IOI Oleochemical, Product specification, Jan. 30, 2018, IOI Oleo GmbH, pp. 1-2, https://azeliscanada.com/wp-content/uploads/2020/09/MIGLYOL_812_N_SPEC-1.pdf (Year: 2018).*
IOI Oleochemical, Technical data sheet, Miglyol 812N (Excipient), Apr. 2017, IOI Oleo GmbH Pharma, p. 1-5 (Year: 2017).*
Garidel Patrick et al., "High-concentration protein formulations: How high is high?," European Journal of Pharmaceutics and Biopharmaceutics, Elsevier Science Publishers B.V., Amsterdam, NL, vol. 119, Jul. 6, 2017, pp. 353-360.
Shire Steven J. et al., "Challenges in the development of high protein concentration formulations," Journal of Pharmaceutical Sciences, American Pharmaceutical Association, US, vol. 93, No. 6, Jun. 1, 2004, pp. 1390-1402.
International Search Report PCT Application No. PCT/US2019/062596, International Filing Date Nov. 21, 2019, Date of Mailing Mar. 3, 2020.

* cited by examiner

*Primary Examiner* — Abigail Vanhorn
*Assistant Examiner* — Ali S Saeed
(74) *Attorney, Agent, or Firm* — Kramer Levin Naftalis & Frankel LLP

(57) ABSTRACT

The present invention pertains to compositions and methods of making high concentration protein formulations of a therapeutic protein.

15 Claims, 8 Drawing Sheets

FIG. 1

Suspension Properties
- Solid content
- Vehicle composition
- Colloidal stability

Device (Syringe/Needle) Properties
- Needle gauge
- Dispensing speed
- Needle design

Spray dried powder Properties
- Particle size / distribution
- Formulation (excipients & composition)
- Spray drying process parameters (effecting excipient distribution within particle)

FIG. 5

Impact of Suspension Concentration

[Bar chart showing Dispensing Force (N) Plateau on y-axis (0-35) versus mg spray dried powder per mL vehicle on x-axis. Two bars: 397 (~23 N with error bar) and 516 (~30 N).]

■ mAb1 in BA+Miglyol (50/50 v/v)

HIGH CONCENTRATION PROTEIN FORMULATION

FIELD

The present invention pertains to compositions and methods of making high concentration protein formulations of a therapeutic protein.

BACKGROUND

There are numerous benefits to using subcutaneous administration for biopharmaceuticals, including high concentration protein formulations. The advantages of subcutaneously administered formulations include: (i) the ability for self-administration, (ii) ease of use, (iii) reduction of hospitalization and thus treatment costs, and (iv) increased patient compliance. These benefits are especially important in the treatment of chronic diseases such as asthma, psoriasis, or arthritic diseases. As a result, there has been an increase in marketed biopharmaceuticals that rely on subcutaneous administration.

There are many challenges, however, in successfully developing high concentration protein formulations for subcutaneous administration including the physico-chemical properties of the formulations, the stability of the therapeutic protein in the formulation, the correlation between protein aggregation and solution concentration, and physical limitations in volume and injection force for subcutaneous drug delivery devices. Further, therapeutic proteins, such as antibodies and receptor Fc-fusion proteins should be formulated in a manner that not only makes the molecules suitable for administration to patients, but also maintains their stability during storage and while at the site of administration.

Thus, there is a need to overcome the challenges which have, thus far, limited the availability of high concentrations protein formulations, based on volumetric contribution of the protein.

SUMMARY

The present invention pertains to compositions and methods of making high concentration protein formulations of a therapeutic protein. More particularly, the present invention generally pertains to compositions and methods of making high concentration protein formulations having at least 200 mg/mL therapeutic protein with an injection glide force of less than about 50 Newton (N). These formulations are particularly suitable for subcutaneous administration.

The present invention satisfies the need for high concentration protein formulation comprising at least 200 mg/mL of a therapeutic protein by overcoming the challenges traditionally associated with high concentration protein formulations. The high concentration protein formulation of the present invention may comprise an appropriate vehicle in addition to the therapeutic protein. For example, in certain embodiments of the present invention, the high concentration protein formulation may comprise: (i) a therapeutic protein; (ii) a hydrophobic agent; and (iii) a viscosity-reducing agent.

For example, in one exemplary embodiment, the high concentration protein formulation may comprise: (i) at least 200 mg/mL therapeutic protein; (ii) 25%-75% v/v hydrophobic agent; and (iii) 25%-75% v/v viscosity-reducing agent. The hydrophobic agent may be selected from SASOL, sunflower oil, Castor Oil, Glycerol, ethyl oleate, triglycerides, or combinations thereof. The triglycerides may be selected from Glyceryl Tricaprylate/Tricaprate (Miglyol 812, Miglyol 810, Miglyol 818, Miglyol 829, Miglyol 840, CAPTEX 300, CAPTEX INJ 300, CAPTEX INJ 335 and like), Glyceryl Tricaprylate, and triacetin, or combinations thereof. In one exemplary embodiment, the hydrophobic agent is Miglyol 812 N. The viscosity-reducing agent may be selected from ethanol, benzyl alcohol, benzyl benzoate, ethyl acetate, N-Methyl-2-pyrrolidone, ethyl lactate, PEG400, or combinations thereof. In one exemplary embodiment, the viscosity-reducing agent is benzyl alcohol. In another aspect of this embodiment, the high concentration protein formulation may comprise more than one triglyceride.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof. The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation may comprise additives to increase the dispersibility of the formulation. The additive is selected from polyvinyl alcohol, trileucine, or any other known polymer with low water-solubility, or combinations thereof.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof.

The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation exhibits an injection force of less than about 50 N, or less than 40 N, or less than 35, or less than 30 N, or less than 25 N, or less than 20 N.

In one exemplary embodiment of the present invention, the high concentration protein formulation comprises: (i) at least about 200 mg/mL of therapeutic protein; (ii) about 25% to about 75% Miglyol 812 N; and (iii) about 25% to about 75% benzyl alcohol.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof. The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation exhibits an injection force of less than about 50 N, or less than 40 N, or less than 35, or less than 30 N, or less than 25 N, or less than 20 N.

In another exemplary embodiment of the present invention, the high concentration protein formulation comprises: (i) at least about 200 mg/mL of therapeutic protein; (ii) about 25% to about 75% Miglyol 812 N; and (iii) about 25% to about 75% ethanol.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof. The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation exhibits an injection force of less than about 50 N, or less than 40 N, or less than 35, or less than 30 N, or less than 25 N, or less than 20 N.

In another exemplary embodiment of the present invention, the high concentration protein formulation comprises: (i) at least about 200 mg/mL of therapeutic protein; (ii) about 25% to about 75% Miglyol 810N; and (iii) about 25% to about 75% benzyl alcohol.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof. The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation exhibits an injection force of less than about 50 N, or less than 40 N, or less than 35, or less than 30 N, or less than 25 N, or less than 20 N.

In another exemplary embodiment of the present invention, the high concentration protein formulation comprises: (i) at least about 200 mg/mL of therapeutic protein; (ii) about 25% to about 75% triacetin; and (iii) about 25% to about 75% benzyl alcohol.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof. The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation exhibits an injection force of less than about 50 N, or less than 40 N, or less than 35, or less than 30 N, or less than 25 N, or less than 20 N.

In another exemplary embodiment of the present invention, the high concentration protein formulation comprises: (i) at least about 200 mg/mL of therapeutic protein; (ii) about 25% to about 75% triglyceride; and (iii) about 25% to about 75% benzyl alcohol.

In one aspect of this embodiment, the therapeutic protein in the high concentration protein formulation is micronized to optimize syringability and/or stability. In one exemplary embodiment, the micronized protein is produced by spray drying. The concentration of the protein as a micronized solid protein powder in the high concentration protein formulation is between about 200 mg/mL to about 600 mg/mL, preferably between about 300 mg/mL to about 600 mg/mL, more preferably between about 400 mg/mL to about 600 mg/mL.

In one aspect of this embodiment, the therapeutic protein in the micronized protein powder contained in the high concentration protein formulation is formulated with excipients. For example, the excipients in the high concentration protein formulation may include (i) a carbohydrate; (ii) an amino acid; and (iii) a non-ionic surfactant. The carbohydrate may be selected from sucrose, mannitol, sorbitol, dextran, maltodextrin, trehalose, or combinations thereof. The amino acid may be selected from proline, histidine, isoleucine, methionine, cysteine, glycine, arginine, lysine, L-leucine, Tri-leucine, alanine, glutamic acid, aspartic acid, L-threonine, 2-phenylamine, or combinations thereof. The non-ionic surfactant may be selected from polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof.

In one aspect of this embodiment, the high concentration protein formulation exhibits an injection force of less than about 50 N, or less than 40 N, or less than 35, or less than 30 N, or less than 25 N, or less than 20 N.

The high concentration protein formulations of the present invention may be contained within any suitable container useful for storing pharmaceutical formulations. Examples of such suitable containers include, e.g., glass or plastic vials, syringes and cartridges. The container may be clear or opaque (e.g., amber colored). In certain exemplary embodiments, the vials or syringes are coated with silicone, such as silicone dioxide. In certain exemplary embodiments, the headspace in the vials is filled with an inert gas to displace any oxygen present that may have an adverse effect on stability of the antibody. Such inert gas may be selected from nitrogen or argon. In one exemplary embodiment, the high concentration protein formulation may be contained in a pre-filled syringe.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 1 is an exemplary summary of factors impacting protein stability and syringability of high concentration suspension formulations according to an embodiment of the present invention.

represent a vehicle comprising ethanol in Miglyol 812N; the data points with cross (✚) represents the vehicle with 25% ethanol, 25% PEG400 and 50% Miglyol 812N; and the data points open circles (○) represent a vehicle comprising ethanol in Miglyol 810N. The Y-axis depicts the dispensing force in Newton (N).

Figure 4:
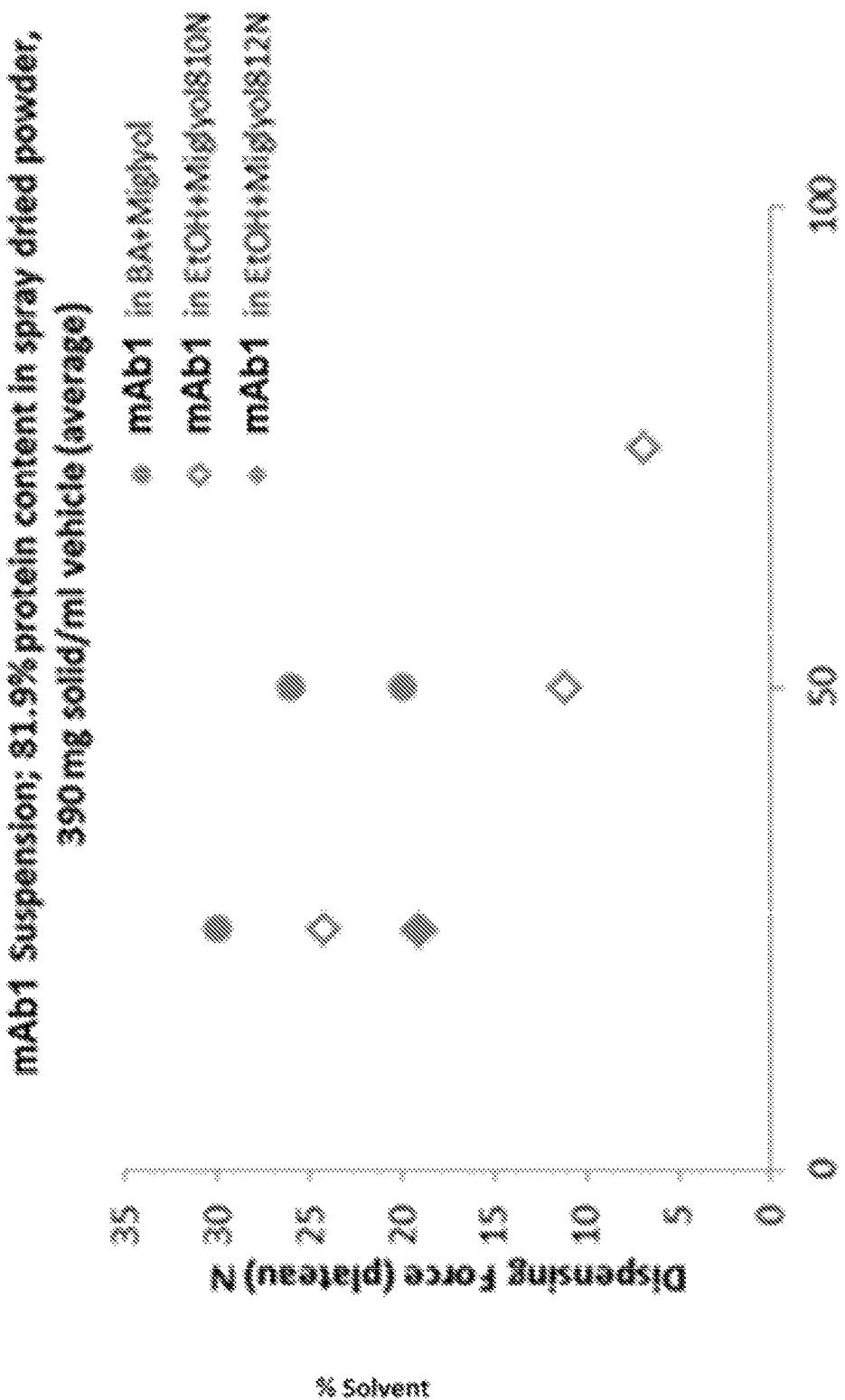

FIG. 4 is a scatter graph illustrating the dispensing force for high concentration suspensions containing mAb1 prepared according to an exemplary embodiment of the present invention. The X-axis depicts the percentage of the viscosity reducing agent (solvent) in the vehicle (as % solvent). The data points with closed circles (●) represent a vehicle comprising benzyl alcohol in Miglyol 812N; the data points with closed diamonds (♦) represent a vehicle comprising ethanol in Miglyol 812N; and the data points with open diamonds (◊) represent a vehicle comprising ethanol in Miglyol 810N. The Y-axis depicts the dispensing force in Newton (N).

FIG. 5 is a bar graph illustrating the impact of micronized protein powder suspension concentration on dispensing force for high concentration suspensions containing mAb1 prepared according to an exemplary embodiment of the present invention. The X-axis represents the weight in mg of the spray dried powder per mL of the vehicle. The Y-axis depicts the dispensing force in Newton (N).

FIG. 6 is a bar graph illustrating the behavior of different protein powders on the syringability. The Y-axis depicts the dispensing force in Newton (N).

FIG. 7 is a bar graph illustrating the physical stability of mAb1 in suspension vehicles prepared according an exemplary embodiment of the present invention. The X-axis depicts the different viscosity reducing agents (e.g., solvent): control sample with Miglyol 812N and no viscosity reducing agent (e.g., solvent); with vehicle comprising 25% ethanol (EtOH) in Miglyol 812N; vehicle comprising 25% ethyl lactate (EL) in Miglyol 812N; a vehicle comprising 25% benzyl benzoate (BB) in Miglyol 812N as three independent preparations; a vehicle comprising 75% benzyl alcohol in Miglyol 812N. The Y-axis depicts the relative percentage of the protein mAb1 having native conformation (expected hydrodynamic radius) at 1 day at room temperature by size-exclusion ultra-high performance chromatography (SEC-UPLC).

FIG. 8 is a line graph illustrating the stability of a therapeutic protein in vehicle prepared according to an exemplary embodiment of the present invention. The X-axis depicts the incubation time at room temperature in hours. The data points with open squares (□) represent a formulation of mAb1 in vehicle comprising 50% v/v benzyl alcohol and Miglyol 812N; the data points with closed diamonds (♦) represent a formulation of mAb3 in vehicle comprising 50% v/v benzyl alcohol and Miglyol 812N; and the data points with closed circles (●) represent a formulation of mAb2 in vehicle comprising 50% v/v benzyl alcohol and Miglyol 812N. The Y-axis depicts the relative percentage of the protein mAb1 having native conformation (expected hydrodynamic radius) by SEC-UPLC.

DETAILED DESCRIPTION

It should be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

There are numerous benefits to using subcutaneous administration for biopharmaceuticals, such as, the ability for self-administration, ease of use, reduction of hospitalization and thus treatment costs, and increased patient compliance. Furthermore, as proteins are typically more stable in the solid state than solution and minimal molecular interactions are expected in the solid state between protein particles, proteins can be expected to be more stable in such a high concentration suspension compared to an equivalently high concentration solution. There are many challenges, however, in successfully developing high concentration protein formulations for subcutaneous administration (Das et al. (2015) "Commercializing High-Concentration mAbs." BioPharm International 29(11): 47-49; Johnson, B., & Rostovtsev, A (2017) "High Concentration Biologic Formulations: Challenges and Solutions. Drug Discov. Develop." p. Online; S. J., S., Shahrokh, Z., & Liu, J. (2004) "Challenges in the development of high protein concentration formulations." J. Pharm. Sci. 93(6): 1390-1402).

For subcutaneous administration, viscosity and protein stability can be primary limitations for viable high concentration protein formulations (e.g., >200 mg/mL), particularly in regards to manufacturing and processing considerations, storage stability, as well as compatability with pre-filled syringe dosing devices. For example, therapeutic proteins (e.g., antibodies) in a formulation are prone to degradation, aggregation and/or undesired chemical modifications unless the solution is formulated properly. The stability of a protein in a formulation depends not only on the kinds of excipients used in the formulation, but the amounts and proportions of those excipients relative to one another along with the concentration of the soluble protein.

Because of these challenges, most of the commercially approved monoclonal antibody drug products are formulated at low concentration of protein (e.g., below 100 mg/ml) and administered intravenously through infusions, especially for oncology (Wang (1999) "Instability, stabilization, and formulation of liquid protein pharmaceuticals." Intl. J. Pharm. 185, 129-188; Shire (2004) "Formulation and manufacturability of biologics." Curr. Opin. Biotechnol. 20 (6), 708-714; Garidel and Bassarab (2008) In Quality for Biologics: Critical Quality Attributes, Process and Change Control, Production Variation, characterization, Impurities and Regulatory Concerns pp. 94-113. Publishing, London, UK). Thus, there is need to overcome the challenges which have, thus far, limited the availability of high concentrations protein formulations, based on volumetric contribution of the protein. (Garidel et al. "High-concentration protein formulations: how high is high?" Eur. J. Pharm. and Biopharm. (2017) 119: 353-360; Johnson, B., & Rostovtsev, A (2017, Jun. 29) "High Concentration Biologic Formulations: Challenges and Solutions." Drug Discov. Develop. p. Online).

The development of a high concentration protein formulation of a therapeutic protein requires evaluation of protein stability, solution viscosity, vehicle toxicity, along with injection force. There remains a need in the art for such high concentration protein formulations which can supply at least 200 mg/mL of a protein while maintaining stability for subcutaneous administration to patients.

The development of highly concentrated protein formulations above 200 mg/mL can be associated with a number of challenges, which have been discussed extensively in the art, for example in: Shire (2004) "Formulation and manufacturability of biologics." Curr. Opin. Biotechnol. 20 (6), 708-714; Warne et al. (2011) Development of high concentration protein biopharmaceuticals: The use of platform approaches in formulation development. Eur. J. Pharm.

Biopharm. 78, 208-212; Garidel et al. (2015) Prediction of colloidal stability of high concentration protein formulations. Pharm Dev. Technol. 20(3), 367-374; Allmendinger et al. (2015) Sterile Filtration of Highly Concentrated Protein Formulations: Impact of Protein Concentration, Formulation Composition, and Filter Material. Pharm. Biotechnol. 104, 3319-3329).

There are a few key factors that may be considered for the compostions and methods of making high concentration protein formulations. The first is the choice of vehicle. The vehicle can have an effect on the rheological and syringe-baility properties of high concentration protein formulations. The majority of vehicles combine a hydrophobic agent with a viscosity reducing agent. It may be important that protein and formulation excipients are negligibly soluble in both components to ensure protein stability. Vehicle choice and the ratio of viscosity reducing agent to hydrophobic agent may depend on several factors, including protein stability, solution viscosity, colloidal stability, and vehicle toxicity.

The present invention includes identifying a vehicle composition that is suitable for preparing high concentration protein formulations and in which the therapeutic protein is stable. The criteria used for evaluating vehicles include protein stability and recovery after 3-24 hours at room temperature (e.g., the duration of time required to suspend and administer) and the injection force (e.g., at the plateau) required to dispense the suspension through a 27 g TW needle in a 1 mL BD Hypak pre-filled syringe (PFS). The rationale for the limited stability is that at the very least the therapeutic protein must be stable when suspended and administered in the vehicle. While the formulation would ideally be loaded and stored in a PFS, there are other potential approaches to formulation that can be used including suspension in the hydrophobic agent for storage and addition of the viscocity reducing agent to reduce viscosity just prior to administration, or suspension in the hydrophobic agent/viscocity reducing agent vehicle just prior to administration using a custom device. The vehicle composition with hydrophobic agent and viscosity reducing agent serves a distinct purpose. The hydrophobic agent ensures a suspension with colloidal stability both during storage and administration and the viscosity reducing agent acts to reduce the viscosity.

In some exemplary embodiments, the hydrophobic agent selected from SASOL, sunflower oil, Castor Oil, Glycerol, ethyl oleate, triglycerides, or combinations thereof. In some embodiments, the hydrophobic agent is a triglyceride, such as, but not limited to, Miglyol 810 N, Miglyol 812 N, triacetin, or combinations thereof and the viscosity-reducing agent is selected from ethanol, benzyl alcohol, ethyl acetate, N-Methyl-2-pyrrolidone, or combinations thereof.

The second factor to consider for compostions and methods of making high concentration suspension formulations is the physical properties of the therapeutic protein. An optimized formulation in this context has a high protein content and minimal excipients in order to maximize protein concentration in the suspension. Colloidal instability of high concentrated protein formulations is more pronounced at higher concentrations (Wagner et al. (2012) Colloids and Surfaces: Physicochem. Eng. Aspects 415, 421-430; Shire (2004) "Formulation and manufacturability of biologics." Curr. Opin. Biotechnol. 20 (6), 708-714; Warne et al. (2011) "Development of high concentration protein biopharmaceuticals: The use of platform approaches in formulation development." Eur. J. Pharm. Biopharm. 78, 208-212; Garidel et al. (2015) "Prediction of colloidal stability of high concentration protein formulations." Pharm Dev. Technol. 20(3), 367-374; and Wagner et al. (2012) "The electrokinetic potential of therapeutic proteins and its modulation: Impact on protein stability" Colloids and Surfaces: Physicochem. Eng. Aspects 415, 421-430). In certain cases, to overcome protein stability, freeze-dried formulations were developed for high-concentration formulation as an alternative to liquid formulations (Cao et al. (2013) "Rational design of lyophilized high concentration protein formulations-mitigating the challenge of slow reconstitution with multidisciplinary strategies" Eur. J. Pharm. Biopharm. 85, 287-293). However, it was observed that the reconstitution times of freeze-dried high concentration protein formulations are extremely prolonged, up to 30 minutes and longer (Garidel et al. (2015) "Stability of buffer-free freeze-dried formulations: A feasibility study of a monoclonal antibody at high protein concentrations" Eur. J. Pharm. Biopharm. 97, 125-139).

While spray drying has emerged as a feasible approach to stablize proteins, other methods for stabilzing proteins also can be utlized. The physical properties of the protein and corresponding colloidal properties of the formulation can depend on the processes such as spray drying. For example, it has been shown that increasing particle size in the micron range can in fact decrease injection force, particularly at higher suspension concentrations (see, e.g., U.S. Pat. No. 9,072,668), and it has been demonstrated in silico that hemispherical particles are expected to disperse slower than spherical particles for a given injection force and are more likely to clog a needle during dispensing than spherical particles of the same size and composition. (Whitaker et al. (2011) "Particle size and shape effects in medical syringe needles: experiments and simulations for polymer microparticle injection." Mater Sci: Mater Med, 22: 1975-1983). While these reports refer specifically to colloidal suspensions dispensed through medical devices, there also exists a variety of research on how powder properties, particle size, and suspending liquid impact fluid properties of colloidal suspensions. For example, a paper published in the journal Powder Technology investigating colloidal suspensions in the context of dredging equipment highlights how at increasing particle size in the 15-40 μm range the dependence of suspension viscosity on solid content decreases and the propensity for shear thickening at high suspension concentrations decreases with increasing smaller particles (6 μm). (Konijin et al (2014) "Experimental study of the viscosity of suspensions: effect of solid fraction, particle size and suspending liquid." Powder Technology 266:61-59). A summary of the factors impacting protein stability in and syringability of high concentration protein formulations is provided in FIG. 1.

Several additives can improve the dispersibility of the spray dried protein particles and the selection of these additives depends on the therapeutic protein and the amount of therapeutic protein in the formulation. For example, the additives may include amino acids, carbohydrates, surfactants and/or water-soluble polymers.

The present invention is not limited to particular methods and experimental conditions described, as such methods and conditions may vary. It is also to be understood that the terminology used herein is for the purpose of describing particular embodiments, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

Definitions

Terms used herein shall be accorded the following meanings to provide context and are not intended to change or limit the ordinary and customary meaning, unless otherwise indicated elsewhere herein.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

Development of high concentration protein formulation results in several manufacturing, stability, analytical, and delivery challenges. The high concentration protein formulation of the present invention attempts to overcome the challenge.

High Concentration Protein Formulations

As used herein, the term "high-concentration" means a final concentration of at least about 200 mg/mL of a therapeutic protein in the formulation. In exemplary embodiments, the high concentration of the therapeutic protein could be about 200 mg/mL or greater.

As used herein, the term "protein formulation" refers to a therapeutic protein that is formulated together with one or more pharmaceutically acceptable vehicles. In some embodiments, the therapeutic protein is present in a unit dose amount appropriate for administration in a therapeutic regimen.

As used herein, the term "suspension" refers to a formulation in which negligibly soluble solid particles are dispersed throughout a second phase, the vehicle which is generally a liquid. The term suspension describes dispersion without reference to the particle size of the solid material. However, the particle size of the solid material can affect both its physical and chemical behavior, so a distinction is usually made between a colloid or colloidal suspension with a particle size range of up to about 1 µm and a 'coarse dispersion' with larger particles. The term suspension used herein covers both these suspension types, in addition to the suspensions with solid particles generally in the range of about 0.1 µm to about 10 µm. Suspensions are composed of multiple particles which leads to multiple particulate interactions. These interactions can, to some extent, be thought of as the interactions of the diffuse layers around individual particles and hence the electrical double layer provides the basis for understanding inter-particulate interactions. The behavior of particles in suspension is complex, even when only two individual interacting particles are considered; the behavior ultimately being dependent on the relative contribution of the repulsive and attractive energies at any separation distance. The radius of the particle appears to affect both the attractive and repulsive energies. It can be relatively easily controlled by milling or micronization of larger particles to achieve a desired small particle size, or by crystal engineering techniques, intended to produce small particles directly from a solution.

As used herein, the term "protein" includes any amino acid polymer having more than about 50 amino acids covalently linked via amide bonds. Proteins contain one or more amino acid polymer chains, generally known in the art as "polypeptides." A protein may contain one or multiple polypeptides to form a single functioning biomolecule. "Polypeptides" generally contain over 50 amino acids, whereas "peptides" generally contain 50 amino acids or less.

As used herein, "therapeutic protein" includes any of proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), and mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," 28 Biotechnol Genet Eng. Rev. 147-75 (2012). In some exemplary embodiments, proteins contain modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

In certain exemplary embodiments of the present invention, the high concentration protein formulation comprises (i) at least 200 mg/mL of therapeutic protein and (ii) vehicle. The "vehicle" can be a carrier in which the therapeutic protein is formulated and/or administered. The vehicle can include a hydrophobic agent, viscosity-reducing agent, water, or combinations thereof.

In certain embodiments of the present invention, the high concentration protein formulation comprises (i) at least 200 mg/mL of therapeutic protein; (ii) hydrophobic agent; and (iii) viscosity-reducing agent.

As used herein, the term "hydrophobic agent" refers to a material having a hydrophilic-lipophilic balance (HLB) value of 0-13. Exemplary hydrophobic agents are vegetable oils, fatty acids having 8-24 carbons, wax, biodegradable polymers, and amphiphilic materials. Exemplary vegetable oils are almond oil, anise oil, apricot kernel oil, arachis oil, argan oil, avocado oil, borage oil, cajuput oil, canola oil, caraway oil, cassia oil, castor oil, cinnamon oil, citronella oil, clove oil, coconut oil, coriander oil, corn oil, cottonseed oil, eucalyptus oil, evening primrose oil, fennel oil, geranium oil, grapeseed oil, hazelnut oil, hemp oil, jojoba oil, juniper oil, lavender oil, lemon oil, macadamia oil, mace oil, melaleuca oil, neem oil, neroli oil, niaouli oil, nutmeg oil, olive oil, orange oil, palm oil, palm kernel oil, pine oil, poppyseed oil, pulegium oil, pumpkin seed oil, rapeseed oil, rice bran oil, rosehip oil, rosemary oil, rue oil, safflower oil, sesame oil (SO), spearmint oil, soybean oil, sunflower oil, thyme oil, walnut oil or wheatgerm oil. Exemplary fatty acids are caprylic acid, capric acid, lauric acid, myristic acid, palmitic acid, stearic acid, arachidic acid, linoleic acid, myristoleic acid, palmitoleic acid, sapienic acid, oleic acid, a-linolenic acid, arachidonic acid, eicosapentaenoic acid, erucic acid, docosahexaenoic acid, eicosapentaenoic acid, docosahexaenoic acid, docosapentaenoic acid, and glyceride (monoglyceride; diglyceride; triglyceride) with different chain lengths. Exemplary biodegradable polymers are polylactic acid (PLA), polyglycolic acid (PGA), polylactic-co-glycolic acid (PLGA), poly c-caprolactone (PCL), polyorthoesters, polyhydroxybutyrate (PHB), polydioxanone, polyanhydrides, polytrimethylene carbonate, and polyphosphazenes. Exemplary amphiphilic materials are a polyethoxylated castor oil or derivative thereof (collectively referred to as a "polyethoxylated castor oil"), a polyoxyethylene alkyl ether, a polyoxyethylene sorbitan fatty acid ester, a polyoxyethylene stearate, a block copolymer of polyethylene oxide ("PEO")—polypropylene oxide ("PPO")—PEO, a block copolymer of PPO-PEO-PPO, a tetra-functional block copolymer of PEO-PPO, such as (PEO-PPO)$_2$—(PPO-PEO)$_2$, or a tetra-functional block copolymer of PPO-PEO, such as (PPO-PEO)$_2$—(PEO-PPO)$_2$. The amount of hydrophobic agent present in the formulations can range from about 0.2% to 99.9%, for example 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

As used herein, the term "triglyceride" refers to an ester derived from glycerol and three fatty acids. Exemplary triglycerides are Glyceryl Tricaprylate/Tricaprate (Miglyol 812, Miglyol 810, Miglyol 818, Miglyol 829, Miglyol 840, CAPTEX 300, CAPTEX INJ 300, CAPTEX INJ 335 and like), Glyceryl Tricaprylate, and triacetin.

"Viscosity" as used herein may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity," sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, "a viscosity reducing agent" refers to an agent that, when present in a vehicle or formulation, reduces the viscosity or injection force of the vehicle or formulation compared to the viscosity or injection force of a vehicle or formulation lacking the viscosity reducing agent. The amount of viscosity reducing agent present in the reduced viscosity vehicles or formulations of the invention can range from about 0.2% to about 99.9% of the formulation, for example 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. The viscosity reducing agent can reduce the viscosity or injection force of a vehicle or a formulation by at least 5%, for example 5%, 10%, 15%, 20%, 25%, 30%, 35%, 40%, 45%, 50%, 55%, 60%, 65%, 70%, 75%, 80%, 85%, or 90%. The non-limiting, exemplary viscosity reducing agents are diethyl sebacate, diethylene glycol monoethyl ether, ethyl acetate, ethyl oleate (EO), isopropyl myristate, linoleic acid, propionic acid, triethyl citrate, propylene glycol, ethanol, propanol, isopropanol, polyethylene glycol, polyperfluoroethers, fluorocarbon (halothane, methoxyflurane, enflurane, isoflurane, sevoflurane and desflurane, etc.), fluorinated ketone, perfluorodecalin, perfluoroacrylate, perfluoromethacrylate, benzyl alcohol, lauryl alcohol, perfluorodecalin, N-Methyl-2-pyrrolidone, glycofurol, polyethylene glygol (PEG), alkyl ketone, lower alkyl ester of citric acid, benzyl benzoate, methyl benzoate, ethyl benzoate, n-propyl benzoate, isopropyl benzoate, butyl benzoate, isobutyl benzoate, sec-butyl benzoate, tert-butyl benzoate, and isoamyl benzoate. The term "solvent" as used herein is used interchangeably with "viscosity-reducing agent."

The terms "non-aqueous high concentration protein formulation," "high concentration protein formulation," "high concentration protein formulation," and "high concentration suspension formulation" are used interchangeably.

In certain exemplary embodiments of the present invention, the high concentration protein formulation may include an additional ingredient or excipient. "Excipients" include various substances used for various purposes including buffering, solubilizing, stabilizing, wetting, and/or protecting the protein, and for maintaining or adjusting tonicity of the formulation, stabilizing the formulation chemically and physically. Examples of such excipients are well known in the art.

In certain embodiments of the present invention, the therapeutic protein in high concentration protein formulation is practically insoluble in the vehicle. "Practically insoluble" as used herein refers to a solubility of less than about 1 mg in 10,000 mL.

Degradation of therapeutic protein in high concentration protein formulation is one of the major challenges faced during the development of these formulations. Proteins are less susceptible to chemical degradation in colloid state, compared to liquid state. As a result, the therapeutic protein contained in solid state affords higher stability to the high concentration protein formulation. In certain embodiments of the present invention, the therapeutic protein in high concentration protein formulation is present as a micronized solid protein formulation, produced by spray drying. Protein particles can be reduced in size by micronization. As used herein, the term "micronization" is used to describe size reduction technique where the resulting particle size distribution is less than about 50 μm. The high concentration protein formulation can be prepared by any of the known micronization methods, such as, but not limited to, in-situ micronization, milling, high pressure homogenization, spray drying, and supercritical fluid (SCF). As used herein, the term "micronized solid protein formulation" is a solid formulation comprising a protein and which can be suspended in a vehicle to prepare the high concentration protein formulation. The terms "solid formulation" and "micronized solid protein formulation" are used interchangeably. In addition to the protein, the micronized solid protein formulation can include solvents, additives, amino acids, excipients, thermal stabilizers, and diluents.

As used herein, "spray drying" is a technique that transforms a fluid state into a dried particulate form by spraying it into a hot drying medium. Spray drying can be performed by spray dryer, such as, but not limited to single-stage spray dryer, two-stage spray dryer, short form spray dryer, and tall form spray dryer. Some exemplary embodiments comprise a formulation comprising a micronized solid protein which is produced by spray drying. Preferred exemplary embodiments comprise the spray dried protein in the form of a powder. The disclosed powders of the micronized solid protein provide several advantages including, but not limited to, increases in suspension stability, uniform particle size, and improved dispersibility. The physical properties of the protein particles, and corresponding colloidal properties of the suspension, depend heavily on the spray drying process and on the formulation (Vehring, R. (2008) "Pharamceutical particle engineering via spray drying" 25(5): 999-1022). In some exemplary embodiments, the micronized solid protein formulation comprises a carbohydrate, an amino acid and a surfactant. Exemplary carbohydrates are sucrose, mannitol, sorbitol, dextran, maltodextrin, or trehalose. The amount of carbohydrate in the micronized solid protein formulation can range from about 0.01 to about 50%, for example, about 0.01%, about 0.05%, about 0.1%, about 0.5%, about 1%, about 5%, about 10%, about 15%, about 20%, about 25%, about 30%, about 35%, about 40%, about 45%, or about 50%. Exemplary amino acids are proline, histidine, isoleucine, methionine, cysteine, glycine, arginine, lysine, leucine, tri-leucine, alanine, glutamic acid, aspartic acid, threonine, and 2-phenylamine. The amount of amino acids in the micronized solid protein formulation can range from about 0.01 to about 20%, for example, about 0.01%, about 0.05%, about 0.1%, about 0.5%, about 1%, about 2%, about 3%, about 4%, about 5%, about 10%, about 15%, or about 20%. Exemplary non-ionic surfactants are polysorbate 20 (PS-20), polysorbate 28, polysorbate 40 (PS-40), polysorbate 65, polysorbate 80 (PS-80), polysorbate 81, polysorbate 85, poloxamer 181, poloxamer 188, poloxamer 407, Triton X-100, Brij-35, Brij-30, Tween 20, Tween 80, digitonin, alkyl glycosides (Ri-O—$(CH_2)_x$—R, where R is independently $CH_3$ or cyclohexyl ($C_6H_n$); Ri is independently glucose or maltose; and x=3-15), Pluronic F127, or combinations thereof. The amount of non-ionic surfactant in the micronized solid protein formulation can range from about 0.01% to about 5%, for example, about 0.01%, about 0.02%, about 0.03%, about 0.04%, about 0.05%, about 1%, about 1%, about 3%, about 4%, or about 5%.

In order to maintain an uniform high concentration protein formulation, the micronized solid protein formulation should remain dispersible in the vehicle over time. As used herein, "dispersibility" is used to describe the degree of dispersion of a powder into individual particles or agglomerates upon exertion of an external dispersion force. The traditional approach to improving the dispersibility of cohesive powders is to blend them with excipients or additives that modify the interparticle forces. In some embodiments, the micronized solid protein formulation comprises a spray dried protein powder which includes additives to improve the dispersibility of the spray dried particles. Exemplary additives which improve dispersibility of the spray dried particles are amino acids, lecithin, magnesium stearate, Starch, Sodium Carboxymethyl cellulose, Sodium alginate, Polyethylene glycol, (PEG), Polyvinyl pyrrolidone (PVP), Hydroxy propyl methyl cellulose, (HPMC), Polyvinyl alcohol (PVA), b-Cyclodextrin, Mannitol, Chitosan, Carrageenan, Polyethylene oxides (PEO)/Polypropylene glycol (PPG) copolymers, PEGmodified starches, Vinyl acetate/vinylpyrrolidone random copolymers, Polyacrylic acid and Polyacrylates, ammonium carbonate, albumin, trileucine, surfactants, or carbohydrates. In exemplary embodiments, the additives used to prepare the micronized solid protein, in the form of a spray dried protein powder, and are selected from trileucine, amino acids, polyvinyl alcohol, polyethylene glycol, water soluble polymers, or combinations thereof.

Stability of the High Concentration Protein Formulation

The stability of a high concentration protein formulation can comprise evaluating the chemical stability, physical stability or functional stability. The formulations of the present invention typically exhibit high levels of protein stability. The term "stable," as used herein in reference to the formulations, means that the proteins within the formulations can retain an acceptable degree of chemical structure or biological function after storage under exemplary conditions defined herein. A formulation may be stable even though the protein contained therein does not maintain 100% of its chemical structure or biological function after storage for a defined amount of time. Under certain circumstances, maintenance of about 90%, about 95%, about 96%, about 97%, about 98% or about 99% of an protein's structure or function after storage for a defined amount of time may be regarded as "stable." Stability can be measured, inter alia, by determining the percentage of native protein that remains in the formulation after storage for a defined amount of time at a defined temperature. The percentage of native protein can be determined by, inter alia, size exclusion chromatography (e.g., size exclusion high performance liquid chromatography [SE-HPLC]), such that native means non-aggregated and non-degraded. An "acceptable degree of stability," as that phrase is used herein, means that at least 90% of the native form of the protein can be detected in the formulation after storage for a defined amount of time at a given temperature. In certain embodiments, at least about 90%, 91%, 92%, 93%, 94%, 95%, 96%, 97%, 98%, 99% or 100% of the native form of the protein can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more.

The defined temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C., or about 45° C. For example, a pharmaceutical formulation may be deemed stable if after 6 months of storage at 5° C., greater than about 95%, 96%, 97% or 98% of native protein is detected by SE-HPLC. A pharmaceutical formulation may also be deemed stable if after 6 months of storage at 25° C., greater than about 94%, 95%, 96%, 97% or 98% of native protein is detected by SE-HPLC. A pharmaceutical formulation may also be deemed stable if after 28 days of storage at 45° C., greater than about 91%, 92%, 93%, 94%, 95%, 96%, 97% or 98% of native protein is detected by SE-HPLC. A pharmaceutical formulation may also be deemed stable if after three months of storage at −20° C., greater than about 96%, 97%, or 98% of native protein is detected by SE-HPLC. A pharmaceutical formulation may also be deemed stable if after three months of storage at −30° C., greater than about 96%, 97% or 98% of native protein is detected by SE-HPLC. A pharmaceutical formulation may also be deemed stable if after three months of storage at −80° C., greater than about 96%, 97% or 98% of native protein is detected by SE-HPLC.

Stability can be measured, inter alia, by determining the percentage of protein that forms in an aggregate within the formulation after storage for a defined amount of time at a defined temperature, wherein stability is inversely proportional to the percent aggregate that is formed. This form of stability is also referred to as "colloidal stability" herein. The percentage of aggregated protein can be determined by, inter alia, size exclusion chromatography (e.g., size exclusion high performance liquid chromatography [SE-HPLC]). An "acceptable degree of stability," as that phrase is used herein, means that at most 6% of the protein is in an aggregated form detected in the formulation after storage for a defined amount of time at a given temperature. In certain embodiments an acceptable degree of stability means that at most about 6%, 5%, 4%, 3%, 2%, 1%, 0.5%, or 0.1% of the protein can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C. or about 45° C. For example, a pharmaceutical formulation may be deemed stable if after six months of storage at 5° C., less than about 3%, 2%, 1%, 0.5%, or 0.1% of the protein is detected in an aggregated form. A pharmaceutical formulation may also be deemed stable if after six months of storage at 25° C., less than about 4%, 3%, 2%, 1%, 0.5%, or 0.1% of the protein is detected in an aggregated form. A pharmaceutical formulation may also be deemed stable if after 28 days of storage at 45° C., less than about 6%, 5%, 4%, 3%, 2%, 1%, 0.5%, or 0.1% of the protein is detected in an aggregated form. A pharmaceutical formulation may also be deemed stable if after three months of storage at −20° C., −30° C., or −80° C. less than about 3%, 2%, 1%, 0.5%, or 0.1% of the protein is detected in an aggregated form.

Stability can also be measured, inter alia, by determining the percentage of protein that forms in an aggregate within the formulation after storage for a defined amount of time at a defined temperature, wherein stability is inversely proportional to the percent aggregate that is formed. This form of stability is also referred to as "colloidal stability" herein. The percentage of aggregated protein can be determined by, inter alia, size exclusion chromatography (e.g., size exclusion high performance liquid chromatography [SE-HPLC]). An:acceptable degree of stability," as that phrase is used herein, means that at most 6% of the protein is in an aggregated form detected in the formulation after storage for a defined amount of time at a given temperature. In certain embodiments an acceptable degree of stability means that at most about 6%, 5%, 4%, 3%, 2%, 1%, 0.5%, or 0.1% of the protein can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C. or about 45° C. For example, a pharmaceutical formulation may be deemed stable if after six months of storage at 5° C., less than about 3%, 2%, 1%, 0.5%, or 0.1% of the protein is detected in an aggregated form. A pharmaceutical formulation may also be deemed stable if after six months of storage at 25° C., less than about 4%, 3%, 2%, 1%, 0.5%, or 0.1% of the protein is detected in an aggregated form. A pharmaceutical formulation may also be deemed stable if after 28 days of storage at 45° C., less than about 6%, 5%, 4%, 3%, 2%, 1%, 0.5%, or 0.1% of the protein is detected in an aggregated form. A pharmaceutical formulation may also be deemed stable if after three months of storage at −20° C., −30° C., or −80° C. less than about 3%, 2%, 1%, 0.5%, or 0.1% of the protein is detected in an aggregated form.

Stability can be also measured, inter alia, by determining the percentage of protein that migrates in a more acidic fraction during ion exchange ("acidic form") than in the main fraction of protein ("main charge form"), wherein stability is inversely proportional to the fraction of protein in the acidic form. While not wishing to be bound by theory, deamidation of the protein may cause the protein to become more negatively charged and thus more acidic relative to the non-deamidated protein (see, e.g., Robinson, N. (2002) "Protein Deamidation" PNAS, 99(8):5283-5288). The percentage of "acidified" protein can be determined by, inter alia, ion exchange chromatography (e.g., cation exchange high performance liquid chromatography [CEX-HPLC]). An "acceptable degree of stability," as that phrase is used herein, means that at most 49% of the protein is in a more acidic form detected in the formulation after storage for a defined amount of time at a defined temperature. In certain exemplary embodiments, an acceptable degree of stability means that at most about 49%, 45%, 40%, 35%, 30%, 25%, 20%, 15%, 10%, 5%, 4%, 3%, 2%, 1%, 0.5%, or 0.1% of the protein can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more.

The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., or about 45° C. For example, a pharmaceutical formulation may be deemed stable if after three months of storage at −80° C., −−30° C., or −20° C. less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the protein is in a more acidic form. A pharmaceutical formulation may also be deemed stable if after six months of storage at 5° C., less than about 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the protein is in a more acidic form. A pharmaceutical formulation may also be deemed stable if after six months of storage at 25° C., less than about 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the protein is in a more acidic form. A pharmaceutical formulation may also be deemed stable if after 28 days of storage at 45° C., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the protein can be detected in a more acidic form.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in OD405 of the formulation is less than about 0.05 (e.g., 0.04, 0.03, 0.02, 0.01, or less) from the OD405 of the formulation at time zero. Measuring the biological activity or binding affinity of the protein to its target may also be used to assess stability. For example, a formulation of the present invention may be regarded as stable if, after storage at e.g., 5° C., 25° C., 45° C., etc. for a defined amount of time (e.g., 1 to 12 months), the protein contained within the formulation binds to its target with an affinity that is at least 90%, 95%, or more of the binding affinity of the protein prior to said storage. Binding affinity may be determined by e.g., ELISA or plasmon resonance. Biological activity may be determined by an protein activity assay, such as e.g., contacting a cell that expresses the protein with the formulation comprising the a protein. The binding of the protein to such a cell may be measured directly, such as e.g., via FACS analysis. Alternatively, the downstream activity of the protein system may be measured in the presence of the protein, and compared to the activity of the protein system in the absence of protein. Additional methods for assessing the stability of a protein in formulation are demonstrated in the Examples presented below.

Containers for High Concentration Protein Formulation

The high concentration protein formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present invention including, e.g., clear and opaque (e.g., amber) glass or plastic vials. Likewise, any type of syringe can be used to contain and/or administer the pharmaceutical formulations of the present invention. The formulation within the container may be treated using any method known in the art to remove oxygen to improve protein stability if necessary. The oxygen in the headspace (the gaseous space above a liquid in a closed container) may be replaced by an inert gas, such as nitrogen or argon.

The high concentration protein formulations can be administered to a patient by parenteral routes such as injection (e.g., subcutaneous, intravenous, intramuscular, intraperitoneal, etc.) or percutaneous, mucosal, nasal, pulmonary and/or oral administration. Numerous reusable pen and/or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen and/or autoinjector delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif), the PUSHCLICK™ (Scandinavian Health Ltd. (SHL) Group), the PENLET™ (Haselmeier, Stuttgart, Germany), the EPIPEN (Dey, L. P.), and the HUMIRA™ Pen (Abbott Labs, Abbott Park, Ill.), to name only a few.

The use of a microinfusor to deliver the high concentration protein formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996), which are incorporated herein in their entirety. Microinfusors are particularly useful for the delivery of large doses of therapeutic proteins contained within high concentration (e.g., about 100, 125, 150, 175, 200 or more mg/mL) and/or viscous solutions.

In certain exemplary embodiments of present invention, a prefilled syringe to deliver the high concentration protein formulation is also contemplated herein. Exemplary syringes available from Vetter GmbH, Ravensburg, Germany; Hamilton Robotics, Nevada, United States of America; Terumo, Tokyo, Japan; or Becton, Dickinson and Company, New Jersey, United States of America. In some exemplary embodiments of present invention, a prefilled syringe can comprise a dual chamber to form the suspension prior to injection. In some embodiments, one of the chambers in the dual chamber can comprise hydrophobic agent and the viscosity-reducing agent and the other can comprise the therapeutic protein. In some other embodiments, the one of the chamber in the dual chamber can comprise therapeutic agent suspended in hydrophobic agent and the other can comprise viscosity-reducing agent.

As used herein "syringeability" refers to the attribute of the formulation that reflects the ease with which the formulation flows through the needle. It can be calculated as the force required for the injection of a solution at a given injection rate via a needle of predetermined gauge and length. The distinct forces terms used to describe syringeability are syringe force, syringe force maximum, and breakout force. As used herein "syringe force" refers to the force required to sustain the movement of the plunger at a constant rate to expel the content of the syringe. The terms "syringe force," "sustained force," "glide force," "injection force," and "dispensing force" can be used interchangeably. Syringe force is hypothesized to be dependent on the solid concentration in suspension, powder properties and dispensing speed. The syringe force can be measured by load cell installed on an Instron system. As used herein, "syringe glide force" refers to the time-averaged force required to maintain the plunger motion at a constant rate on its course to the front end of the syringe. As used herein, "syringe force maximum" refers to the highest force measured before the plunger finishes its course at the front end of the syringe. As used herein "breakout force" refers to the force required to initiate the movement of the plunger. As illustrated in the examples, for most of the high concentrated protein formulations, there is a direct correlation between syringe force maximum and syringe force as determined from Instron data.

In certain exemplary embodiments of the present invention, the syringe force required to push the high concentration protein formulation through a rigid needle shield glass syringe having a 0.25 inch inside diameter, equipped with a 0.5 inch 26½-gauge needle at a 4 mm/second injection speed is less than about 50 N, for example less than about 45 N, less than about 40 N, less than about 35 N, less than about 25 N, or less than about 25 N. In preferred embodiments, the syringe force is less than about 30 N.

Therapeutic Uses of the Pharmaceutical Formulations

The pharmaceutical formulations of the present invention are useful, inter alia, for the treatment, prevention and/or amelioration of a disease or disorder. Exemplary, non-limiting diseases and disorders that can be treated and/or prevented by the administration of the pharmaceutical formulations of the present invention include, infections; respiratory diseases; pain resulting from any condition associated with neurogenic, neuropathic or nociceptic pain; genetic disorder; congenital disorder; cancer; herpetiformis; chronic idiopathic urticarial; scleroderma, hypertrophic scarring; Whipple's Disease; benign prostate hyperplasia; lung disorders, such as mild, moderate or severe asthma, allergic reactions; Kawasaki disease, sickle cell disease; Churg-Strauss syndrome; Grave's disease; pre-eclampsia; Sjogren's syndrome; autoimmune lymphoproliferative syndrome; autoimmune hemolytic anemia; Barrett's esophagus; autoimmune uveitis; tuberculosis; nephrosis; arthritis, including chronic rheumatoid arthritis; inflammatory bowel diseases, including Crohn's disease and ulcerative colitis; systemic lupus erythematosus; inflammatory diseases; HIV infection; AIDS; LDL apheresis; disorders due to PCSK9-activating mutations (gain of function mutations, "GOF"), disorders due to heterozygous Familial Hypercholesterolemia (heFH); primary hypercholesterolemia; dyslipidemia; cholestatic liver diseases; nephrotic syndrome; hypothyroidism; obesity; atherosclerosis; cardiovascular diseases; neurodegenerative diseases; neonatal Onset Multisystem Inflammatory Disorder (NOM ID/CINCA); Muckle-Wells Syndrome (MWS); Familial Cold Autoinflammatory Syndrome (FCAS); familial mediterranean fever (FMF); tumor necrosis factor receptor-associated periodic fever syndrome (TRAPS); systemic onset juvenile idiopathic arthritis (Still's Disease); diabetes mellitus type 1 and type 2; auto-immune diseases; motor neuron disease; eye diseases; sexually transmitted diseases; tuberculosis;disease or condition which is ameliorated, inhibited, or reduced by a VEGF antagonist; disease or condition which is ameliorated, inhibited, or reduced by a PD-1 inhibitor; disease or condition which is ameliorated, inhibited, or reduced by a Interleukin antibody; disease or condition which is ameliorated, inhibited, or reduced by a NGF antibody; disease or condition which is ameliorated, inhibited, or reduced by a PCSK9 antibody; disease or condition which is ameliorated, inhibited, or reduced by a ANGPTL antibody; disease or condition which is ameliorated, inhibited, or reduced by an activin antibody;

disease or condition which is ameliorated, inhibited, or reduced by a GDF antibody; disease or condition which is ameliorated, inhibited, or reduced by a Fel d 1 antibody; disease or condition which is ameliorated, inhibited, or reduced by a CD antibody; disease or condition which is ameliorated, inhibited, or reduced by a C5 antibody or combinations thereof.

Exemplary Formulations

In certain exemplary embodiments of the present invention, the high concentration protein formulation comprise of at least 200 mg/mL of therapeutic protein. For example, formulations described by these exemplary embodiments comprise the therapeutic protein at a concentration of at least, at least about 200 mg/mL, at least about 210 mg/mL, at least about 220 mg/mL, at least about 230 mg/mL at least about 250 mg/mL, at least about 250 mg/mL, at least about 260 mg/mL, at least about 270 mg/mL, at least about 280 mg/mL, at least about 290 mg/mL, at least about 300 mg/mL, at least about 320 mg/mL, at least about 340 mg/mL, at least about 350 mg/mL, at least about 380 mg/mL, at least about 400 mg/mL, at least about 420 mg/mL, at least about 450 mg/mL, at least about 480 mg/mL, at least about 500 mg/mL.

In certain exemplary embodiments of the present invention, the therapeutic protein in high concentration protein formulation is in the form of a micronized solid protein formulation. In preferred embodiments, the micronized solid protein formulation is prepared using a spray drying process. In one aspect, the concentration of protein in the micronized solid protein formulation ranges from 1% to 99%. In another aspect, the concentration of protein in the micronized solid protein formulation is at least about 50%, for example at least about 51%, at least about 52%, for example at least about 53%, at least about 54%, for example at least about 55%, at least about 60%, at least about 65%, at least about 70%, at least about 75%, at least about 80%, at least about 85%, at least about 90%, at least about 95%, at least about 98%, at least about 99%, at least about 99.5%, at least about 99.9%.

Additives can be added during the spray drying process to improve the dispersibility of the micronized solid protein formulation. The additives that may be included in the subject micronized solid protein formulation include amino acids, carbohydrates, surfactants and/or water-soluble polymers. The carbohydrate that may be included in the subject micronized solid protein formulation is selected from mannitol, sucrose, trehalose, maltodextrin, sorbitol, or combinations thereof. The concentration of carbohydrate in the micronized solid protein formulation is less than about 50%, for example less than about 45%, less than about 40%, less than about 35%, less than about 30%, less than about 25%, less than about 20%, less than about 18%, less than about 15%, less than about 12%, less than about 10%, less than about 5%, less than about 2%, less than about 1%, less than about 0.5%, or less than about 0.1%. The amino acid that may be included in the subject micronized solid protein formulation is selected from naturally occurring amino acids and derivatives thereof. In preferred embodiments, the amino acid is selected from histidine, isoleucine, leucine, trileucine, glycine, or combinations thereof. The concentration of amino acid in the micronized solid protein formulation is less than about 20%, for example, less than about 18%, less than about 15%, less than about 12%, less than about 10%, less than about 5%, less than about 3%, less than about 2%, less than about 1.5%, less than about 1.2%, less than about 1.0%, less than about 0.5%, less than about 0.4%, less than about 0.3%, less than about 0.2%, less than about 0.1%, or less than about 0.05%. The surfactant that may be included in the subject micronized solid protein formulation is selected from polysorbate 20, polysorbate 80, polysorbate 60, poloxamer, polyethylene glycol, or combinations thereof. The concentration of surfactant in the micronized solid protein formulation is less than 5%, for example, less than about 5%, less than about 4.5%, less than about 4%, less than about 3.5%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.4%, less than about 0.3%, less than about 0.2% or less than about 0.1%.

In certain exemplary embodiments of the present invention, the therapeutic protein in high concentration protein formulation is delivered by parenteral administration. The formulation may be administrated subcutaneously. In one exemplary embodiment, the formulation may be contained in a pre-filled syringe. Exemplary pre-filled syringes are available from Vetter GmbH, Ravensburg, Germany; Hamilton Robotics, Nevada, United States of America; Terumo, Tokyo, Japan; or Becton, Dickinson and Company, New Jersey, United States of America. The formulation may be pre-loaded in a syringe and thus is injection ready with no mixing or reconstitution.

All literature and patent-document citations herein are incorporated herein by reference in their entirety.

The present invention will be more fully understood by reference to the following Examples. They should not, however, be construed as limiting the scope of the invention

EXAMPLES

Example 1

Suspension Compounding and Loading

The following examples are put forth so as to provide those of ordinary skill in the art with a complete disclosure and description of how to make and use the methods and compositions of the invention, and are not intended to limit the scope of what the inventors regard as their invention Several formulations (Table 1) comprising different vehicles were prepared by following the procedure described below. The exemplary therapeutic proteins used in the formulations are three monoclonal antibodies.

TABLE 1

| Vehicle | Protein | Formulation |
| --- | --- | --- |
| 75% Miglyol 812N, 25% benzyl alcohol | mAb1 | (390 mg/mL micronized solid protein formulation; 82% protein in spray dried powder) |
| 50% Miglyol 812N, 50% benzyl alcohol | | |
| 75% Miglyol 812N, 25% ethanol | | |
| 50% Miglyol 812N, 50% ethanol | | |
| 75% Miglyol 810N, 25% ethanol | | |
| 50% Miglyol 810N, 50% ethanol | | |
| 25% Miglyol 810N, 75% ethanol | | |
| 50% Miglyol 812N, 50% benzyl alcohol | mAb1 | (397 mg/mL micronized solid protein formulation) |
| 50% Miglyol 812N, 50% benzyl alcohol | mAb1 | (516 mg/mL micronized solid protein formulation) |

TABLE 1-continued

| Vehicle | Protein | Formulation |
|---|---|---|
| 50% Miglyol 812N, 50% benzyl alcohol | mAb1 | (35% w/v micronized solid protein formulation) |
| 50% Miglyol 812N, 50% benzyl alcohol | mAb2 | (29% w/v micronized solid protein formulation) |
| 50% Miglyol 812N, 50% benzylalcohol | mAb3 | (36% w/v micronized solid protein formulation) |
| 75% Miglyol 812N, 25% benzyl alcohol | mAb3 | (274 mg/mL of protein in the formulation; 0.82 w/w protein content in micronized solid protein formulation; 0.335 w/w micronized solid protein formulation in the high concentration protein formulation) |
| 50% Miglyol 812N, 50% benzyl alcohol | mAb3 | (304 mg/mL of protein in the formulation; 0.82 w/w protein content in micronized solid protein formulation; 0.355 w/w micronized solid protein formulation in the high concentration |
| 75% Miglyol 812N, 25% benzyl alcohol | mAb1 | (231 mg/mL of protein in the formulation; 0.82 w/w protein content in micronized solid protein formulation; 0.291 w/w micronized solid protein formulation in the high concentration protein formulation) |
| 50% Miglyol 812N, 50% benzyl alcohol | mAb1 | (232 mg/mL of protein in the formulation; 0.82 w/w protein content in micronized solid protein formulation; 0.286 w/w micronized solid protein formulation in the high concentration protein formulation) |
| 50% Miglyol 812N, 50% benzyl alcohol | mAb1 | (278 mg/mL of protein in the formulation; 0.82 w/w protein content in micronized solid protein formulation; 0.342 w/w micronized solid protein formulation in the high concentration protein formulation) |
| 50% Miglyol 812N, 50% benzyl alcohol | mAb2 | (232 mg/mL of protein in the formulation; 0.80 w/w protein content in micronized solid protein formulation; 0.285 w/w micronized solid protein formulation in the high concentration protein formulation) |
| Miglyol 812 N | mAb1 | 400-500 mg/mL w micronized solid protein formulation (82% w/w mAb1) |
| 75% Miglyol 812N, 25% ethanol | | |
| 75% Miglyol 812N, 25% ethyl oleate | | |
| 75% Miglyol 812N, 25% benzyl alcohol | | |
| 75% Miglyol 812N, 25% benzyl benzoate | | |
| 50% Miglyol 812N, 50% benzyl alcohol | | |
| 25% Miglyol 812N, 75% benzyl alcohol | | |
| 75% Miglyol 812N, 25% benzyl alcohol | mAb3 | (274 mg of protein in the formulation; 0.78 w/w protein content in micronized solid protein formulation; 0.335 w/w micronized solid protein formulation in the high concentration protein formulation plus 0.05 w/w trileucine) |
| 50% Miglyol 812N, 50% benzyl alcohol | mAb3 | (304 mg of protein in the formulation; 0.78 w/w protein content in micronized solid protein formulation; 0.355 w/w micronized solid protein formulation in the high concentration protein formulation plus 0.05 w/w trileucine) |

Vehicles comprised of oil and solvent were compounded by volume to target compositions. Vehicles were prepared fresh each day to ensure that there was no loss of solvent due to evaporation.

Spray dried protein was weighed into a round bottom Eppendorf 2 mL centrifuge tube. Appropriate vehicle was added by volume to spray dried protein according to a target mass of solid per mL vehicle.

Spray dried powder was mixed into the vehicle by vigorous vortexing (vortex, invert and vortex, repeat). After vortexing, sample was briefly placed in centrifuge to spin down suspension from walls of tube to bottom. Too much centrifuging was avoided to prevent phase separation of the suspension. After centrifuging, the sample was sonicated for 1-2 minutes, and if necessary mixing procedure was repeated.

Suspensions were back-loaded into the 1 mL glass syringe using either a spatula, for the more viscous paste-like suspensions, or a pipette for the less viscous suspensions. For dispensing using the Instron, the distance was targeted to be about 10 mm and thus an adequate amount of suspension to allow for 10 mm distance dispensed was targeted. After backloading into syringe, the needle cap was removed and the plunger was utilized to remove air and push suspension to bottom of the syringe. This was particularly important for the more viscous suspensions that, when back loaded with a spatula, tended to just stick to the sides of the syringe barrel. Prior to dispensing the stopper on the plunger was inspected for any suspension stuck in ridges of stopper during loading process. If the suspension was stuck in the ridges of the stopper, the stopper was replaced with a clean stopper.

Example 2

Identification of Appropriate Non-Aqueous Solvent Systems Suitable as Vehicles for High Concentration Protein Suspensions for Subcutaneous Administration In this set of experiments, all evaluations were carried out based on mAb1 as model protein and syringability through a 1 mL glass syringe fitted with a 27 g TW BD needle and dispensed at 4 mm/s. Miglyol 810N was used for preliminary evaluation. The criteria for an appropriate solvent system was based on syringe force, purity (UP-SEC) of protein reconstituted from suspension in vehicle, and use of vehicle components in approved FDA products for subcutaneous injection. Based on use in FDA approved products (Table 3), N-methyl-2-pyrrolidone and ethanol were identified as appropriate solvents.

TABLE 3

| Solvent | Oil | Concentration Range (v/v solvent) | FDA approved product |
|---|---|---|---|
| Ethyl Acetate | Miglyol 810N | 25%-100% | None |
| N-Methyl-2-pyrrolidone | Miglyol 810N | 25%-100% | Atrigel (0.375 mL N-methyl-2-pyrrolidone); |
| Ethanol | Miglyol 810N | 25%-100% | Faslodex (100 mg/ml Ethanol × 5 mL) |

To study glide force, twelve exemplary formulations were evaluated (FIG. 2). The study showed that neat solvent was likely not suitable as a vehicle due to colloidal instability and protein instability. All three solvents showed a similar reduction in syringe force at 25-50% with additional benefit of Ethanol and N-methyl-2-pyrrolidone in reducing glide force at >50% composition. Maximum viscosity reducing effect for Ethyl acetate-Miglyol was observed with 25% Ethyl acetate. A slight increase in glide force over distance after the breakpoint was observed for Ethyl acetate solutions whereas a steady plateau was observed for N-methyl-2-pyrrolidone or Ethanol solutions and for Miglyol alone. Based on syringe force, all three solvent systems were suitable. For Ethyl acetate/Miglyol, no more than 25% Ethyl acetate was needed, for N-methyl-2-pyrrolidone or Ethanol, increasing solvent concentration as much as possible was optimal for reducing syringe force.

Example 3

Determining the Syringe Force

Figure 2:
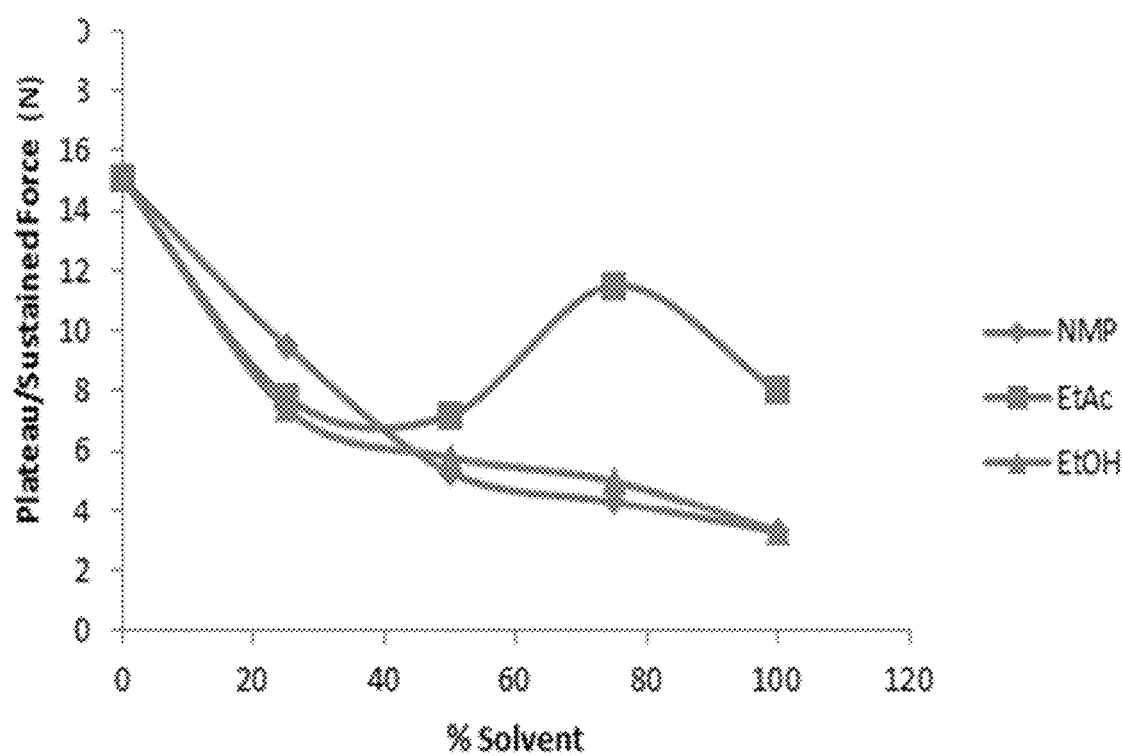
FIG. 2 is a line graph illustrating the glide force in Newton (N) for the vehicles comprising viscosity reducing agent (solvent) in Miglyol 810N. The X-axis depicts the percentage of the viscosity reducing agent (solvent) in the vehicle (as % solvent). The data points with closed diamond (♦) represent a vehicle comprising NMP in Miglyol 810N; the data points with closed squares (■) represent a vehicle comprising ethyl acetate in Miglyol 810N; and the data points with closed triangles (▲) represent a vehicle comprising ethanol in Miglyol 810N. The Y-axis depicts the dispensing force in Newton (N).
Figure 3:
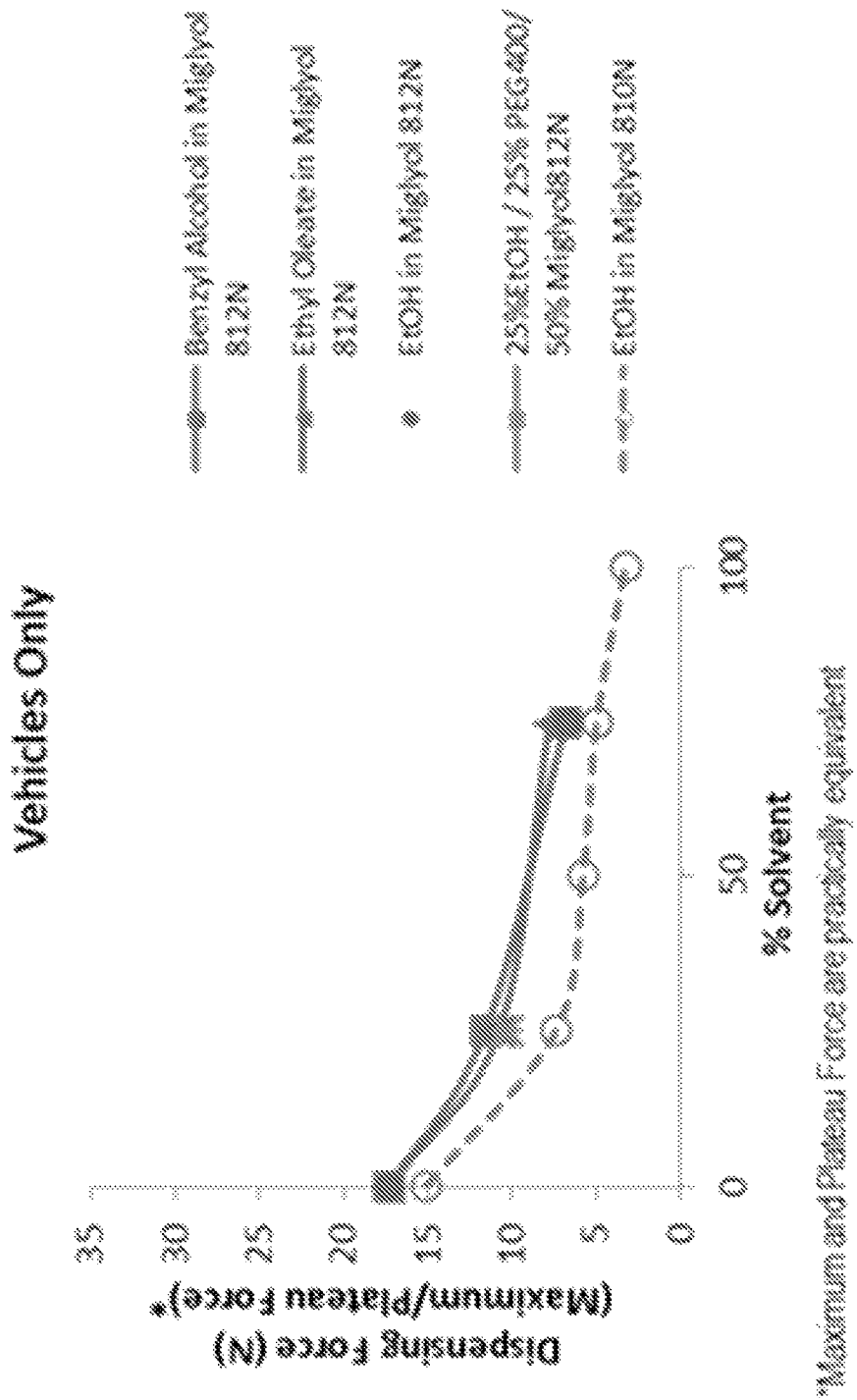
FIG. 3 is a line graph illustrating the dispensing force (e.g., sustained force) for vehicles comprised of hydrophobic agent and viscosity reducing agent (e.g., solvent) according to an exemplary embodiment of the present invention. The X-axis depicts the percentage of the viscosity reducing agent in the vehicle (as % solvent). The data points with closed squares (■) represent a vehicle comprising benzyl alcohol in Miglyol 812N; the data points with closed triangles (▲) represent a vehicle comprising ethyl oleate in Miglyol 812N; the data points with closed circles (●)

Instron was used to determine the syringe force required to dispense suspensions through a 1 mL glass syringe fitted with a 27 g TW needle. Unless otherwise noted, dispensing speed was 4 mm/s and syringe force was reported as the sustained force required for dispensing. In many cases with the formulations prepared following the example 1, the sustained force and maximum force were equivalent—a breakout force was not observed for the way in which these syringes were loaded An initial evaluation of syringe force for different vehicles was performed using 100% Miglyol 810N, 100% Miglyol 812N, 100% ethanol, 25% v/v benzyl alcohol in Miglyol 812N, 75% v/v benzyl alcohol in Miglyol 812N, 25% v/v ethyl oleate in Miglyol 812N, 75% v/v ethyl oleate in Miglyol 812N, 25% v/v ethanol in Miglyol 812N, 75% v/v ethanol in Miglyol 812N, 25% v/v ethanol in Miglyol 810N, 50% v/v ethanol in Miglyol 810N, 75% v/v ethanol in Miglyol 810N, and 25% v/v ethanol with 25% v/v PEG400 in Miglyol 812N. While Miglyol 810N had lower viscosity than Miglyol 812N, Miglyol 812N was favored due to its previous precedent in multiple FDA approved commercial formulations. Ethanol, Benzyl Alcohol, and Ethyl Oleate were all equally effective in reducing syringe force for Miglyol 812N (i.e. viscosity) (FIG. 3).

The dispensing force for high concentration protein formulations was also found to be dependent on the choice of the viscosity-reducing agent and its concentration. In one set of experiments, ethanol was more effective at reducing syringe force in suspensions than benzyl alcohol at the same solvent concentration (FIG. 4). Variability in results at same solvent content may be due to non-uniform mixing and/or actual vs. target solid content in suspension.

The dispensing force for high concentration protein formulations was further found to be dependent on the solid concentration of the therapeutic protein (FIG. 5). In one set of experiments, mAb1 suspension in 50% v/v Benzyl Alcohol in Miglyol 812N demonstrated higher dispensing force with increase in the solid concentration.

Figure 6:
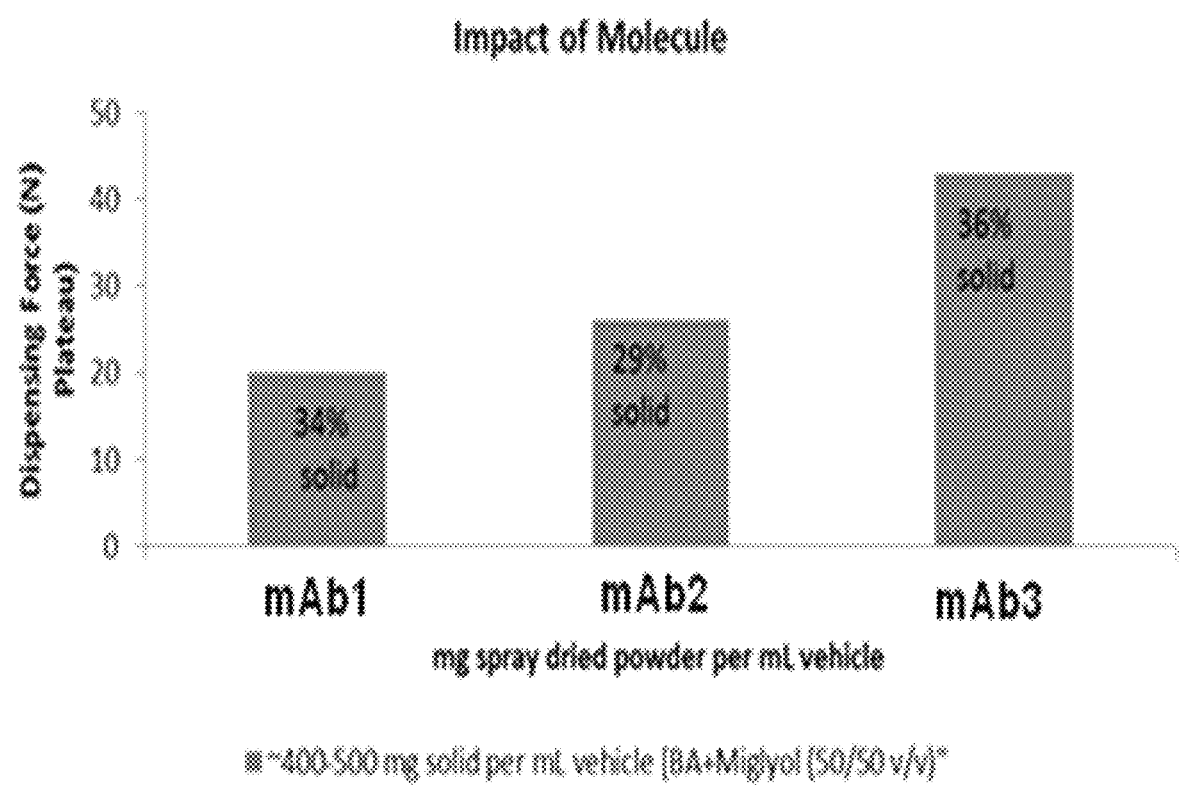
Figure 7:
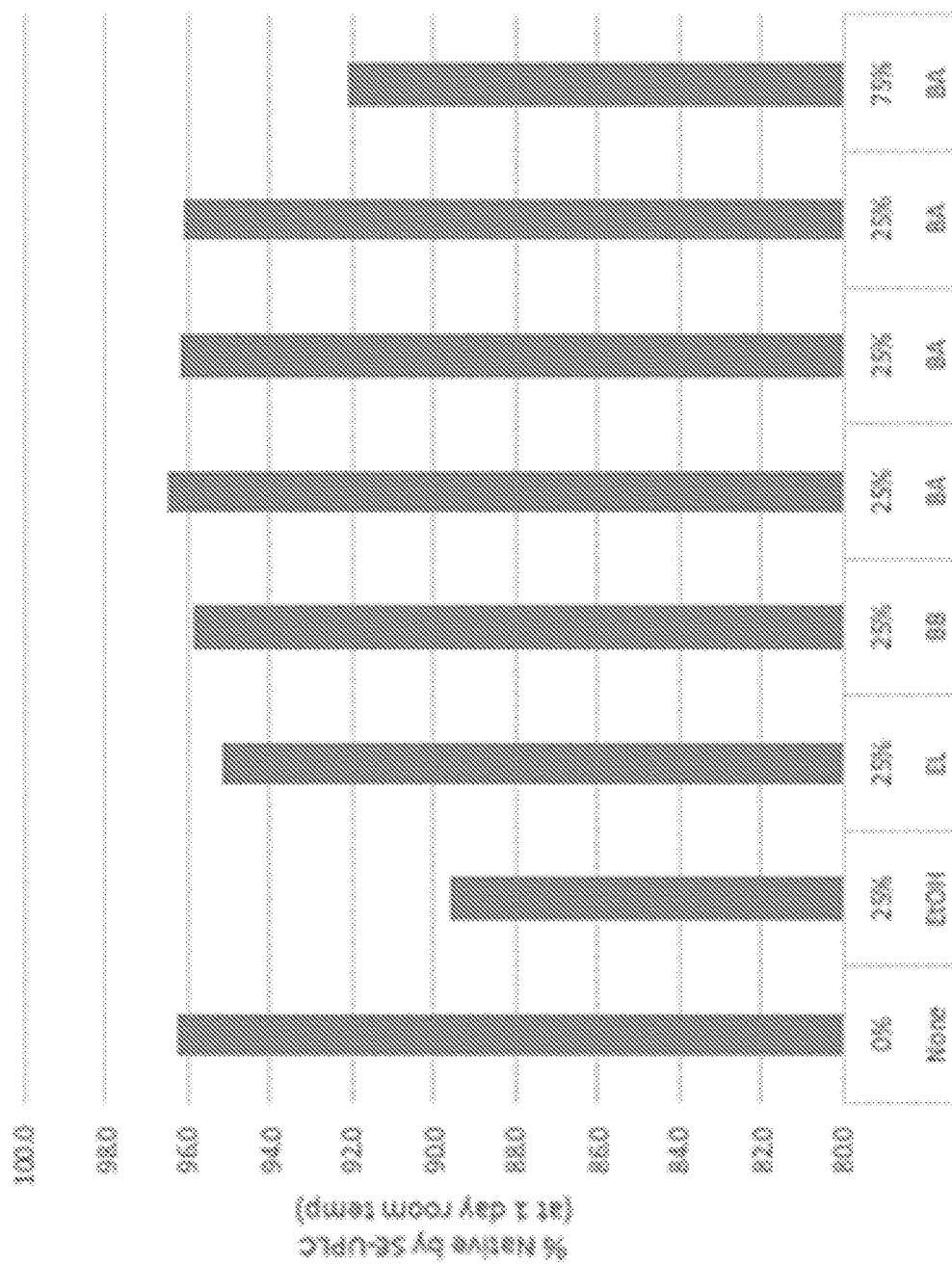
Figure 8:
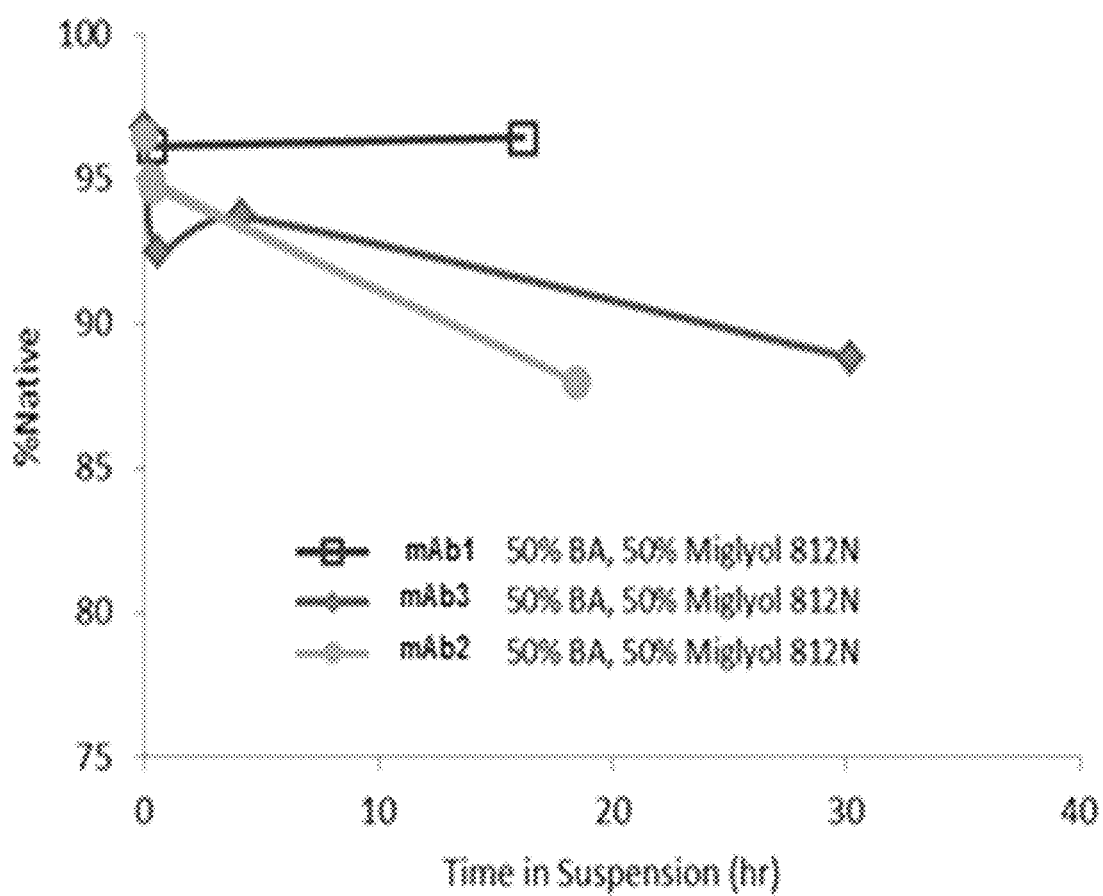

The dispensing force for high concentration protein formulations was also found to be dependent on the powder properties which may be molecule dependent (FIG. 6). Differences in dispensing forces could be due to differences in the molecule's powder properties and/or spray dried particle size, size distribution, and morphology. In one set of experiments, mAb1, mAb2, and mAb3 in same vehicle (benzyl alcohol+Miglyol (50/50 v/v)) demonstrated different dispensing forces. mAb2 at 29% solid concentration demonstrated a higher dispensing force then mAb1 at 34% solid concentration. Syringe force can thus be dependent on solid concentration in suspension, powder properties which may be molecule dependent, and vehicle (Table 2).

TABLE 2

Syringe force of exemplary formulations

| Molecule | Vehicle | Suspension concentration (w/w) | Protein content in Solid (w/w) | Suspension density (mass/volume dispensed, g/mL) | effective protein concentration in suspension (mg/mL) | injection force (N)* |
|---|---|---|---|---|---|---|
| mAb3 | 25% BA | 0.335 | 0.82 | 1.0 (measured) | 274 | 54 |
| mAb3 | 50% BA | 0.355 | 0.82 | 1.0 (measured) | 304 | 43 |
| mAb1 | 25% BA | 0.291 | 0.82 | 1.0 (theoretical) | 231 | 35 |
| mAb1 | 50% BA | 0.286 | 0.82 | 1.0 (theoretical) | 232 | 20.5 |
| mAb1 | 50% BA | 0.342 | 0.82 | 1.0 (theoretical) | 278 | 31 |
| mAb2 | 50% BA | 0.285 | 0.82 | 1.0 (theoretical) | 232 | 27 |

*Injection force at 4 mm/s through 27 g TW BD Hypak 1 mL syringe.

Example 3

Protein Recovery & Stability

The protein recovery and stability of the high concentration protein formulations prepared for use in example 1 were evaluated for long-term stability. Water for injection (WFI) was added to the suspension to target a total of 10 mg/ml or 50 mg/ml as indicated based on the w/w protein content of the suspension determined during compounding and the weight of the suspension sample. Upon addition of WFI to the suspension sample, the sample was gently mixed by swirling/inversion to extract the spray dried protein into the aqueous phase for dissolution. After mixing the sample was centrifuged to separate the aqueous and oil phases (for Miglyol, oil is less dense than water and creates an upper layer). A sample from the aqueous phase was removed and filtered through a 0.22 μm filter to remove any insoluble oil droplets or particulates prior to analysis via UPLC.

In one set of experiments, the test for physical stability in suspension vehicles demonstrated that aggregation was main route of degradation observed (FIG. 7). mAb1 formulation was formulated using mAb1 400-500 mg/mL Spray Dried Powder (81.9% w/w mAb1). The reconstitution was carried out using WFI. A full protein recovery was observed in all samples. mAb1 was more stable in vehicles containing benzyl alcohol than ethanol for a given solvent concentration.

In another set of experiments, stability in suspension was molecule specific (FIG. 8). mAb2 was not stable in 50% BA vehicle for more than 1 hour under ambient conditions, despite a lower suspension concentration; it required a higher dispensing force than mAb1 in the same vehicle.

The "protein recovery" was affected both by heterogeneity of the suspension, which leads to a difference in the actual and theoretical content of protein in the sample, and any loss of protein due to irreversible precipitation or entrapment in the oil phase. In general, this method resulted in full recovery (e.g., ≥90%) of the protein, suggesting that the method for extracting the protein from the oil phase is suitable.

Example 4

Purity (UP-SEC) and Recovery of Protein Reconstituted from Suspension in Vehicle Purity and protein recovery for exemplary formulations were carried out with formulations containing 350 mg/mL mAb1, which were reconstituted using PBS, pH 7.4 at a concentration of 10 mg/mL (Table 4). N-methyl-2-pyrrolidone was not included in results because protein irreversibly precipitated upon reconstitution and was not analyzed further by UP-SEC. Ethyl acetate and Ethanol caused protein aggregation as neat solvents, but in the presence of 75% Miglyol, solvents did not cause any apparent physical degradation of protein (Table 4). Based on protein purity, 25% Ethyl acetate/75% Miglyol and 25% Ethanol/75% Miglyol were selected as suitable solvent systems. Ethanol-Miglyol was one of the solvent systems that met all three criteria for evaluation.

TABLE 4

| Vehicle | % Native | % Recovery |
| --- | --- | --- |
| WFI | 94.6% | 95 |
| Miglyol 810N | 95.0% | 95 |
| Ethyl Acetate | 90.0% | 90 |
| 25% Ethyl acetate; 75% Miglyol | 94.0% | 121 |
| WFI | 95.8% | 96 |
| Ethanol | 91.3% | 96 |
| 25% Ethanol/75% Miglyol | 95.5% | 95 |

What is claimed is:

1. A non-aqueous high concentration protein formulation, comprising:
   a) at least about 200 mg/mL of a therapeutic protein as a micronized solid protein formulation,
   b) a hydrophobic agent comprising glyceryl tricaprylate/tricaprate, and
   c) a viscosity-reducing agent selected from the group consisting of ethanol, benzyl alcohol, ethyl acetate, N-Methyl-2-pyrrolidone, or combinations thereof,
   wherein the formulation has at least 25% v/v of the viscosity-reducing agent and an injection glide force of less than about 30 Newton.

2. The non-aqueous high concentration protein formulation of claim 1, wherein the micronized solid protein formulation is produced by spray drying.

3. The non-aqueous high concentration protein formulation of claim 1, wherein said micronized solid protein formulation has a solubility of less than about 1 mg in 10,000 mL in the hydrophobic agent and the viscosity-reducing agent.

4. The non-aqueous high concentration protein formulation of claim 1, wherein said micronized solid protein formulation is in the form of a powder.

5. The non-aqueous high concentration protein formulation of claim 4, wherein said powder is formulated using trileucine.

6. The non-aqueous high concentration protein formulation of claim 4, wherein the concentration of said powder is between about 200 mg/mL to about 500 mg/mL.

7. The non-aqueous high concentration protein formulation of claim 4, wherein the weight ratio (w/w) of said powder to the non-aqueous high concentration protein formulation is between about 0.250 and 0.700.

8. The non-aqueous high concentration protein formulation of claim 4, wherein said powder comprises the therapeutic protein, a carbohydrate, an amino acid, or a non-ionic surfactant.

9. The non-aqueous high concentration protein formulation of claim 8, wherein the carbohydrate is sucrose, mannitol, or trehalose.

10. The non-aqueous high concentration protein formulation of claim 8, wherein the amino acid is histidine or proline.

11. The non-aqueous high concentration protein formulation of claim 8, wherein the non-ionic surfactant is a polysorbate.

12. The non-aqueous high concentration protein formulation of claim 8, wherein the concentration of the protein is at least about 70%.

13. The non-aqueous high concentration protein formulation of claim 1, wherein said therapeutic protein is a monoclonal antibody.

14. A non-aqueous high concentration protein formulation, comprising:
   at least about 200 mg/mL of a therapeutic protein as a micronized solid protein formulation,
   glyceryl tricaprylate/tricaprate, and
   benzyl alcohol,
   wherein the formulation has at least 25% v/v of the viscosity-reducing agent and an injection glide force of less than about 30 Newton.

15. A non-aqueous high concentration protein formulation, comprising:
   a) at least about 200 mg/mL of a therapeutic protein as a micronized solid protein formulation,
   b) a hydrophobic agent comprising glyceryl tricaprylate/tricaprate, and
   c) a viscosity-reducing agent selected from the group consisting of ethanol, benzyl alcohol, benzyl benzoate, ethyl acetate, N-Methyl-2-pyrrolidone, or combinations thereof,
   wherein the formulation has at least 25% v/v of the viscosity-reducing agent wherein the non-aqueous high concentration protein formulation has an injection glide force of less than about 50 Newton (N).

* * * * *